United States Patent
Realyvasquez, Jr. et al.

(10) Patent No.: US 6,596,003 B1
(45) Date of Patent: Jul. 22, 2003

(54) VASCULAR ANASTOMOSIS DEVICE

(75) Inventors: Fidel Realyvasquez, Jr., Palo Cedro, CA (US); Martin J. Weinstein, South Dartmouth, MA (US); Michael A. Valerio, Wrentham, MA (US)

(73) Assignee: Genzyme Corporation, Cambridge, MA (US)

( * ) Notice: Subject to any disclaimer, the term of this patent is extended or adjusted under 35 U.S.C. 154(b) by 327 days.

(21) Appl. No.: 09/605,598

(22) Filed: Jun. 28, 2000

(51) Int. Cl.⁷ ............................................... A61B 17/08
(52) U.S. Cl. ...................................... 606/153; 606/151
(58) Field of Search ................................. 606/151–155, 606/139, 219, 167

(56) References Cited

U.S. PATENT DOCUMENTS

| | | |
|---|---|---|
| 4,214,587 A | 7/1980 | Sakura, Jr. |
| 5,607,444 A | 3/1997 | Lam |
| 5,676,670 A | 10/1997 | Kim |
| 5,695,504 A * | 12/1997 | Gifford et al. ............... 606/139 |
| 5,702,412 A | 12/1997 | Popov et al. |
| 5,817,113 A | 10/1998 | Gifford, III et al. |
| 5,855,312 A * | 1/1999 | Toledano ................. 227/176.1 |
| 5,895,404 A * | 4/1999 | Ruiz .......................... 606/167 |
| 5,904,697 A | 5/1999 | Gifford, III et al. |
| 5,921,995 A | 7/1999 | Kleshinski |
| 5,972,017 A | 10/1999 | Berg et al. |
| 5,976,178 A * | 11/1999 | Goldsteen et al. .......... 606/151 |
| 6,007,544 A | 12/1999 | Kim |
| 6,024,748 A | 2/2000 | Manzo et al. |
| 6,036,704 A | 3/2000 | Yoon |
| 6,036,705 A | 3/2000 | Nash et al. |
| 6,190,397 B1 | 2/2001 | Spence et al. |
| 6,241,743 B1 * | 6/2001 | Levin et al. ................. 606/153 |
| 6,248,117 B1 * | 6/2001 | Blatter ........................ 606/153 |
| 6,497,710 B2 | 12/2002 | Yencho et al. |
| 6,503,259 B2 | 1/2003 | Huxel et al. |

FOREIGN PATENT DOCUMENTS

| | | |
|---|---|---|
| WO | WO 97/27897 | 8/1997 |
| WO | WO 98/19629 | 5/1998 |
| WO | WO 00/09040 | 2/2000 |

* cited by examiner

Primary Examiner—David O. Reip
Assistant Examiner—Jessica R Baxter
(74) Attorney, Agent, or Firm—Richard D. Allison; Thomas J. DesRosier

(57) ABSTRACT

An anastomosis device is provided for making connections between various conduits in the body of a patient. The device includes a first assembly that is threaded through the target conduit of the patient to a desired location. The device then pierces the wall of the target conduit and is then attached to an external assembly that is withdrawn through the wall of the target conduit to draw the desired connector and a graft conduit into the desired position along the wall of the target conduit. Thereafter, the first assembly is separated from the connector and graft conduit. In this invention, the connector may be a stent like device, staples or similar components to secure the graft conduit to the desired location along the wall of the target conduit.

31 Claims, 15 Drawing Sheets

VASCULAR ANASTOMOSIS DEVICE

FIELD OF THE INVENTION

The present invention relates generally to a device and method for surgically performing an anastomosis on a hollow organ and more particularly to a device and method for performing an anastomosis on a blood vessel and even more particularly for performing an end to side type of anastomosis, such as a coronary artery bypass wherein the end of a graft vessel is attached to the side wall of a target vessel, such as the aorta or coronary artery of a patient.

BACKGROUND OF THE INVENTION

Anastomosis is the surgical joining of hollow biological tissues to create an internal communication between them. Vascular surgery often involves creating an anastomosis between blood vessels or between a blood vessel and a vascular graft to create or restore blood flow to essential tissues. Coronary artery bypass graft surgery is a surgical procedure to restore blood flow to ischemic heart muscle whose blood supply has been compromised by occlusion or stenosis of one or more coronary arteries. One method for performing bypass surgery involves harvesting a saphenous vein or other venous or arterial conduit from elsewhere in the body of a patient, or using an artificial conduit, such as one made from DACRON or DACRON and Goretex, tubing, and connecting the conduit from a viable artery, such as the aorta, to the coronary artery downstream of the blockage or narrowing. A graft with both the proximal and distal end portions detached is known as a free graft. A second method of bypass surgery involves rerouting an end portion of a less essential artery, such as the internal mammary artery, from its native location in the chest of the patient to attach the end portion to a coronary artery downstream of the obstruction. This type of graft is known as a pedicled graft.

In the free graft, both ends of the graft are attached to the desired arteries by end to side anastomotic procedures. In the pedicled graft, the distal end portion of the graft is attached to the artery using an end to side anastomosis. As described below, the anastomosis on a free graft includes a proximal anastomosis and a distal anastomosis. The proximal anastomosis involves the attachment of the proximal end of the conduit to the source of blood flow. The distal anastomosis involves the attachment of the distal end portion of the conduit to the destination of the blood flow so as to bypass the obstruction or occlusion. Typically, the proximal anastomosis will involve the attachment of the proximal end portion of the graft to the aorta of the patient and the distal end portion of the conduit will be attached to the coronary artery at a location below the obstruction or occlusion. Preferably, each of these connections will also be end to side connections. Therefore, as described herein, a pedicled graft will involve a distal anastomosis. The anastomosis may also be referred to as a first or second anastomosis. This reference is irrespective of the end portion of the conduit being used and merely refers to the order in which the anastomotic procedure is performed.

At present, the majority of all vascular anastomotic procedures are performed by conventional hand suturing. Suturing an anastomosis is time consuming and difficult. It is important that each anastomosis provide a smooth and open blood flow path for the blood and the attachment must be leak free under relatively high pressures. A completely leak free anastomosis is not always achieved on the first try. Consequently, there is a frequent need to re-suture the anastomosis to close any leaks or remove any flow interruptions that are detected.

The time consuming nature of hand sutured anastomotic procedures is of special concern in bypass surgery because many procedures are performed while the patient is on cardiopulmonary bypass. During this type of procedure, the heart is isolated from the systemic circulation and the heart is stopped from beating. Recent studies have indicated that the rate of post surgical complications may relate to the length of time a patient is on cardiopulmonary bypass. Therefore, an increasing number of surgeons are performing the bypass procedure on patients while the heart is beating. In these procedures, it is important to maintain the heart tissue adjacent to the blood vessel motionless so that the anastomosis may be performed in a timely manner without leaks or interruptions in the flow of blood through the anastomosis. Performing an anastomosis on a beating heart presents a unique challenge to the surgeon because the tissue surrounding the anastomotic site continues to move in a three dimensional manner while the surgeon is attempting to precisely place the sutures for the procedure.

In order to reduce complications relating to the performance of the anastomosis, various stapling devices have been proposed in an effort to provide a consistent and rapid anastomosis. One such device is proposed in U.S. Pat. No. 5,817,113 granted to Gifford et al. In this patent, a stapling device having a staple with an anchoring portion and a coupling portion is proposed to secure an everted portion of the conduit to the target blood vessel. Additionally, a flange member is used to secure the graft to the target vessel in combination with the staple member. Another approach is illustrated in U.S. Pat. No. 5,676,670 granted to Kim. In this patent, a stent-like device is proposed to extend outwardly from the opening in the target vessel to provide a surface for attachment of the conduit thereto. In this procedure, the stent-like member is inserted into the target vessel from the outside surface and then the distal end portion of the stent-like member is disclosed as being expandable to engage the interior surface of the target vessel. U.S. Pat. No. 5,972,017 granted to Berg et al. also discloses the use of a stent-like member or conduit that is attached to the inside of the target vessel and extends outwardly therefrom for the attachment of the graft thereto. U.S. Pat. No. 5,607,444 granted to Lam illustrates a stent-like member that includes a body portion and a deformable flaring portion. The body portion is adapted to fit within the side branch of a blood vessel and the deformable flaring portion is adapted to fit within a bifurcation of a blood vessel to repair a diseased blood vessel at the bifurcated area.

It is submitted that a need remains for a device to perform an anastomosis in L timely and reliable manner. In particular, it is desirable for a method and device that allows the surgeon to perform multiple bypass procedures using various grafts in a less invasive manner, if desired, and in a manner which allows the surgeon to perform the distal and proximal anastomosis using a procedure that reduces the risks to the patient.

SUMMARY OF THE INVENTION

The coronary arteries are typically about 1–2 mm in diameter, and the pumping heart can move these arteries over distances of several millimeters during each heartbeat. Because the movement of even 1 or 2 millimeters can result in a displacement of the grafting site that can substantially interfere with forming an effective anastomosis, it is desirable to restrain movement of the artery at the surgical site in any direction to less than 1 mm and provide a simple and quick way to secure the graft to the target vessel and bypassed artery. The potential for difficulties from inadvertent movement is further minimized with the present invention by piercing the target vessel from the interior.

An advantage of the present invention is that either the proximal or distal anastomosis may be performed first depending on the preference of the surgeon and multiple procedures may be performed.

A further advantage of the present invention is that the need for a "side biting" clamp is eliminated.

The present invention includes a cannula or delivery apparatus for creating one or more bypasses on-demand between an unobstructed blood vessel such as an aorta and an obstructed vessel such as an obstructed coronary artery. The present invention uses a previously excised vascular segment, such as a saphenous vein or internal mammary artery, or an artificial graft as a conduit. The delivery apparatus delivers various components to the desired location in the interior of the target blood vessel and allows for the deployment of the components remote from the distal end portion of the delivery apparatus. An external assembly is also described to attach an end portion of the conduit to the target vessel and then the external assembly, except for a stent-like member and the conduit, are then removed through the target blood vessel.

The present invention also relates to a device and method for performing an anastomosis from the interior of the target vessel. With this invention, the surgeon may perform either the distal anastomosis or proximal anastomosis first and the surgeon has the ability to choose the desired length of the graft during the procedure. Furthermore, it is anticipated that the distal anastomosis and proximal anastomosis may be performed through a common cannula. In one form of the anastomosis device, the anastomosis device and a cannula are passed through the target vessel to the desired wall of the target vessel. A central guide wire is then passed through the wall of the target vessel and a spoon shaped member is positioned securely against the wall of the target vessel. Next, a cutting cap is secured to the central guide wire along the outside of the target vessel. The graft is then positioned over the cutting cap, guide wire and anastomosis site adjacent to the exterior surface of the target vessel. Staples are then released from the spoon shaped member to pass from the interior of the target vessel to the exterior of the target vessel and into the wall of the graft. The staples may then be manually or automatically crimped to securely retain the graft along the wall of the target vessel. The guidewire is then withdrawn to pull the cutting cap through the wall of the target vessel and into the spoon shaped member. Then entire assembly is then withdrawn and the next anastomosis may be performed as desired.

In another embodiment of the present invention, the cannula is placed in a target vessel such as the aorta. The anastomosis device is then passed through the cannula until the distal end portion reaches the desired position along the wall of the target vessel. The central puncture wire is then passed through the interior wall of the target vessel until a portion of the central puncture wire extends beyond the outer surface of the target vessel. In this embodiment, the central puncture wire is pivotally connected to a cap engaging member that encloses the desired puncture area for the anastomosis device so that the movement of the central guide wire may be coordinated from the exterior of the target vessel along the proximal portion of the anastomosis device.

Next, the cutting member of an external assembly is threaded onto the central puncture member. The graft is then attached to the exterior of a proximal portion of a stent-like member and the stent-like member is attached to the cutting member. The external assembly is then drawn towards the cap member so the cutting member pierces the wall of the target vessel. This motion also draws the distal end portion of the stent-like member through the wall of the blood vessel. As with the piercing motion of the central puncture wire, the movement of the external assembly is controlled by movement of a control member located externally of the target vessel along the proximal portion of the anastomosis device. Once the distal end portion of the stent-like member is positioned in a desired location in the interior of the target vessel, the cutting member may be released from the graft and stent-like member of the external assembly to cause the distal end portion of the stent-like member to expand and contact the inner wall of the target vessel. In this position, the distal end portion of the stent-like member is expanded to be positioned adjacent to the inner wall of the target vessel and the middle portion of the stent-like member extends through the wall of the target vessel such that the tissue adjacent to the puncture in the wall of the target vessel contracts against the middle portion of the stent-like member. The distal end portion of the graft surrounds the proximal end portion of the stent-like member. In this embodiment, the seal between the graft and the target vessel is ensured by the seal between the stent-like member and the inner surface of the graft as well as the distal end portion of the stent-like member which causes the end portion of the graft to be drawn against the outer surface of the target vessel.

Figure 1:
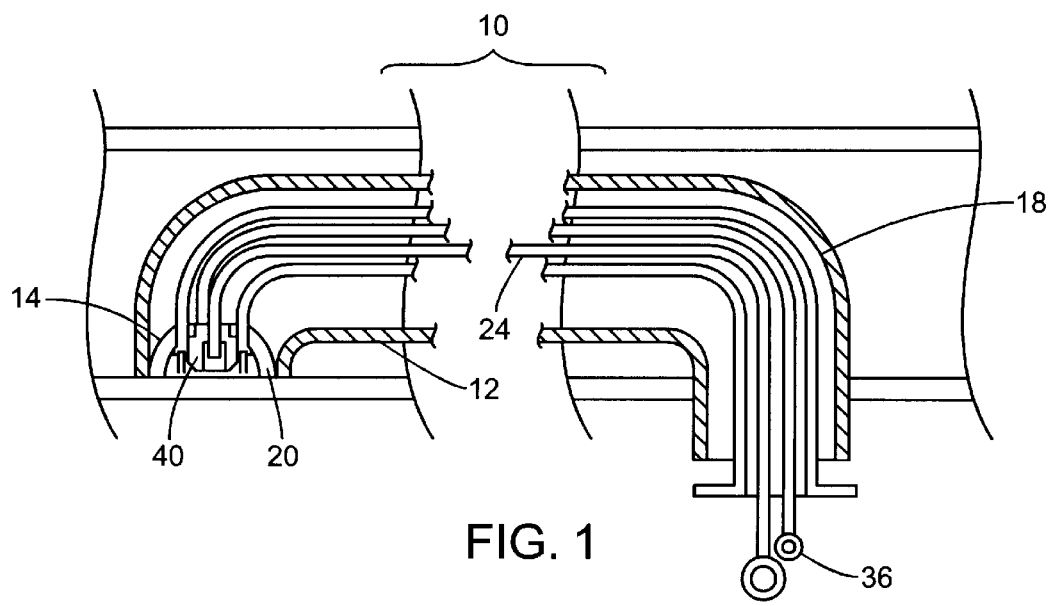
FIG. 1 is a perspective diagrammatical view, partially in cross-section, of a surgical anastomosis device in accordance with a first embodiment of the invention.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 2:
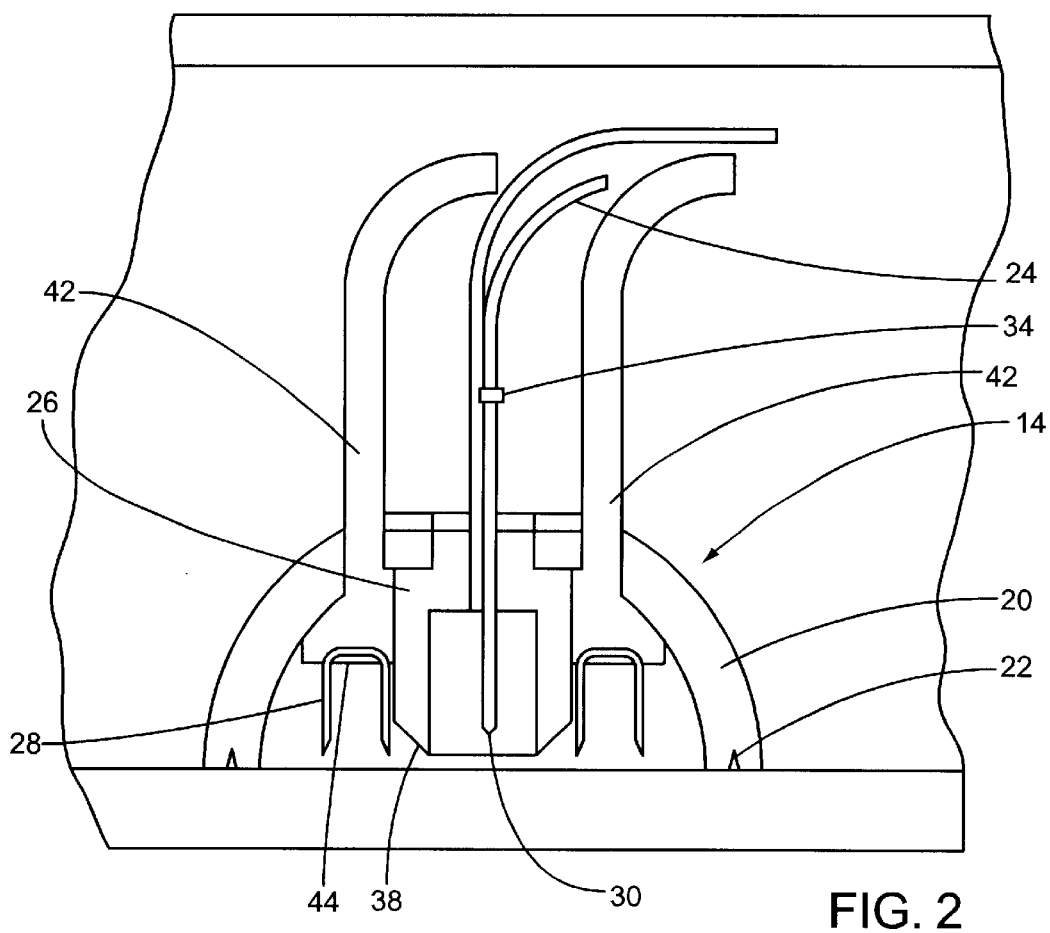
FIG. 2 is an enlarged perspective view of the distal end portion of a surgical anastomosis device illustrating a surgical procedure in accordance with the first embodiment.
Figure 3:
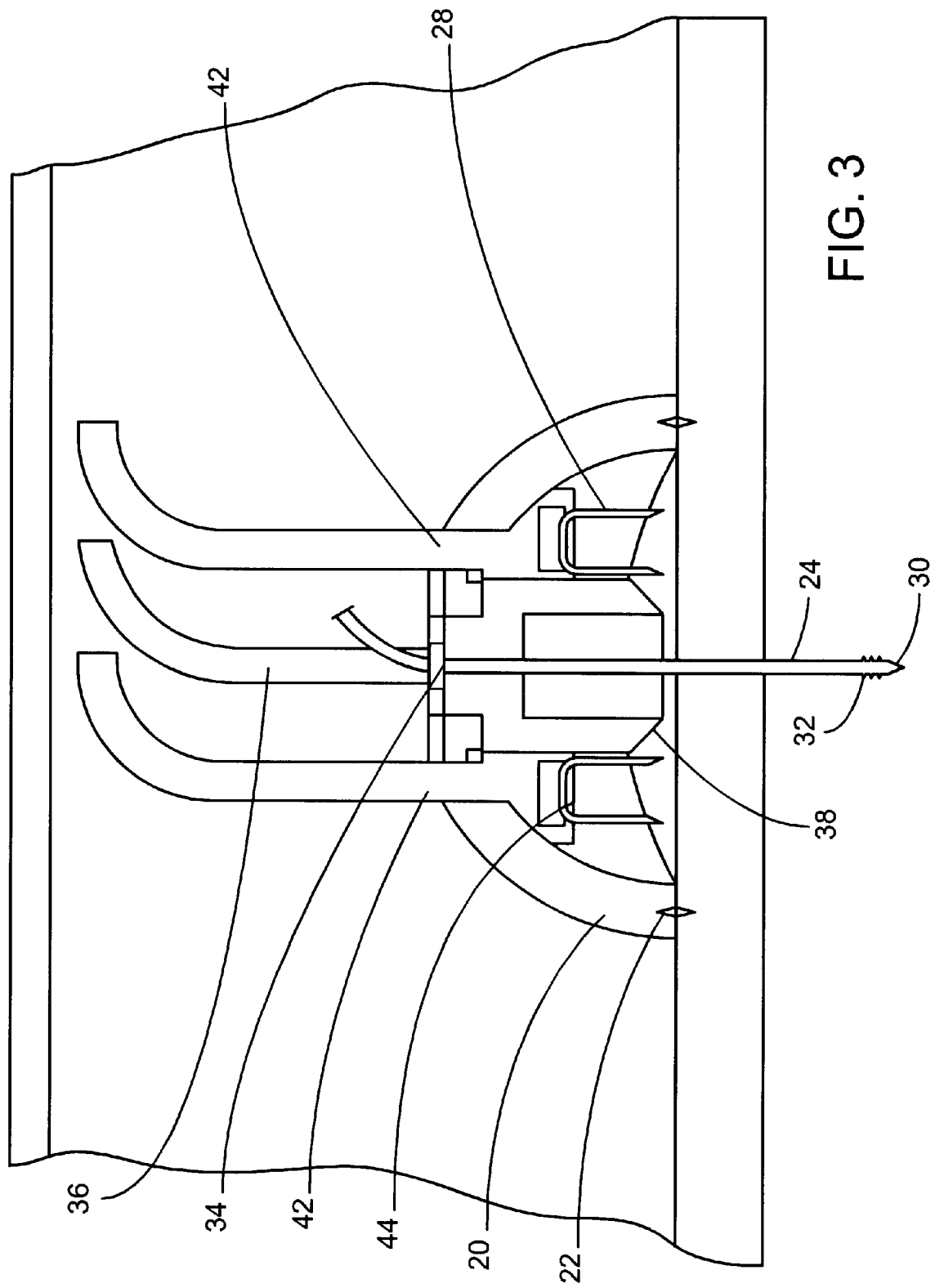
FIG. 3 is a perspective view of the distal end portion of a surgical anastomosis device illustrating a step in the surgical procedure in accordance with the first embodiment.
Figure 4:
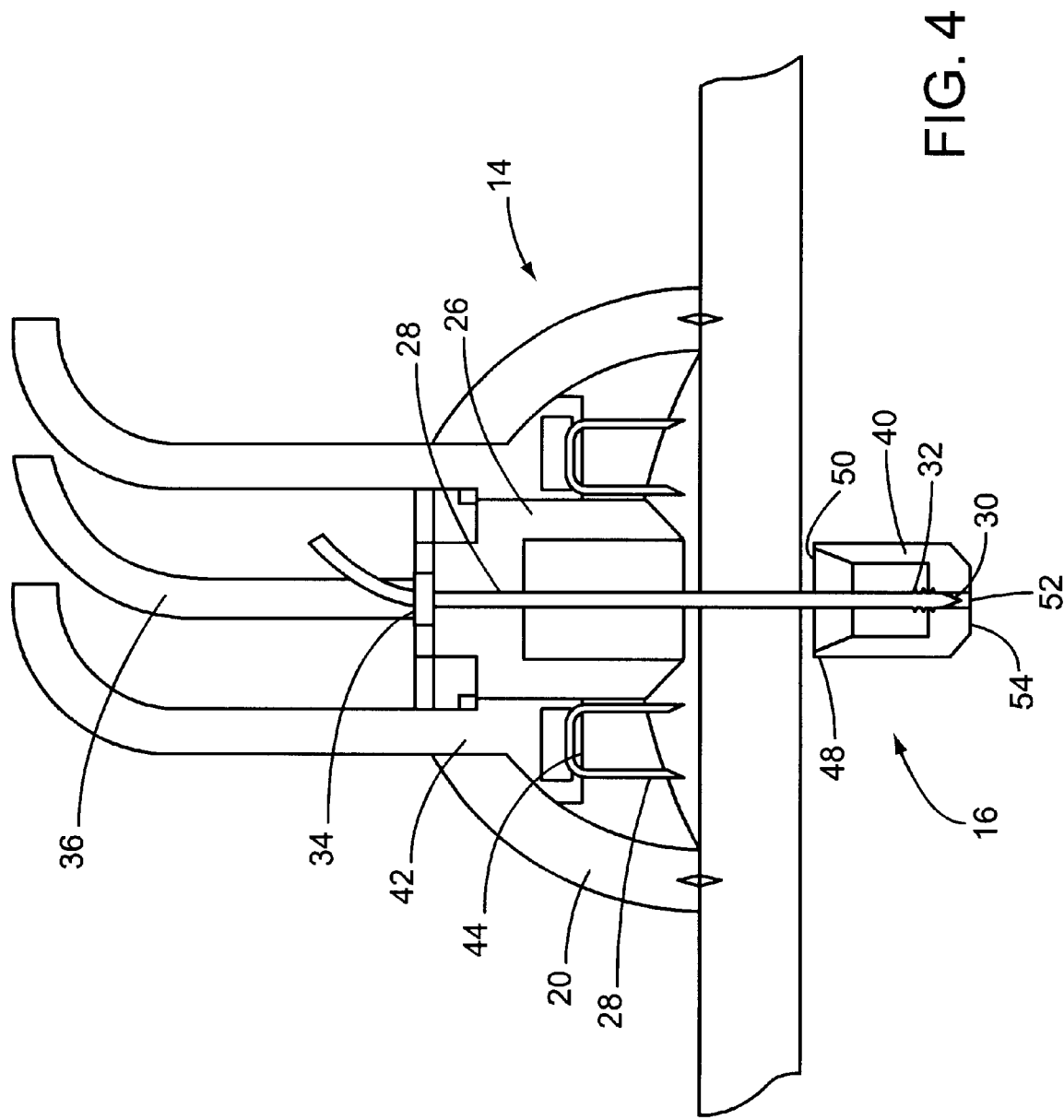
FIG. 4 is a perspective view of the distal end portion of a surgical anastomosis device illustrating a further step in the surgical procedure in accordance with the first embodiment.
Figure 5:
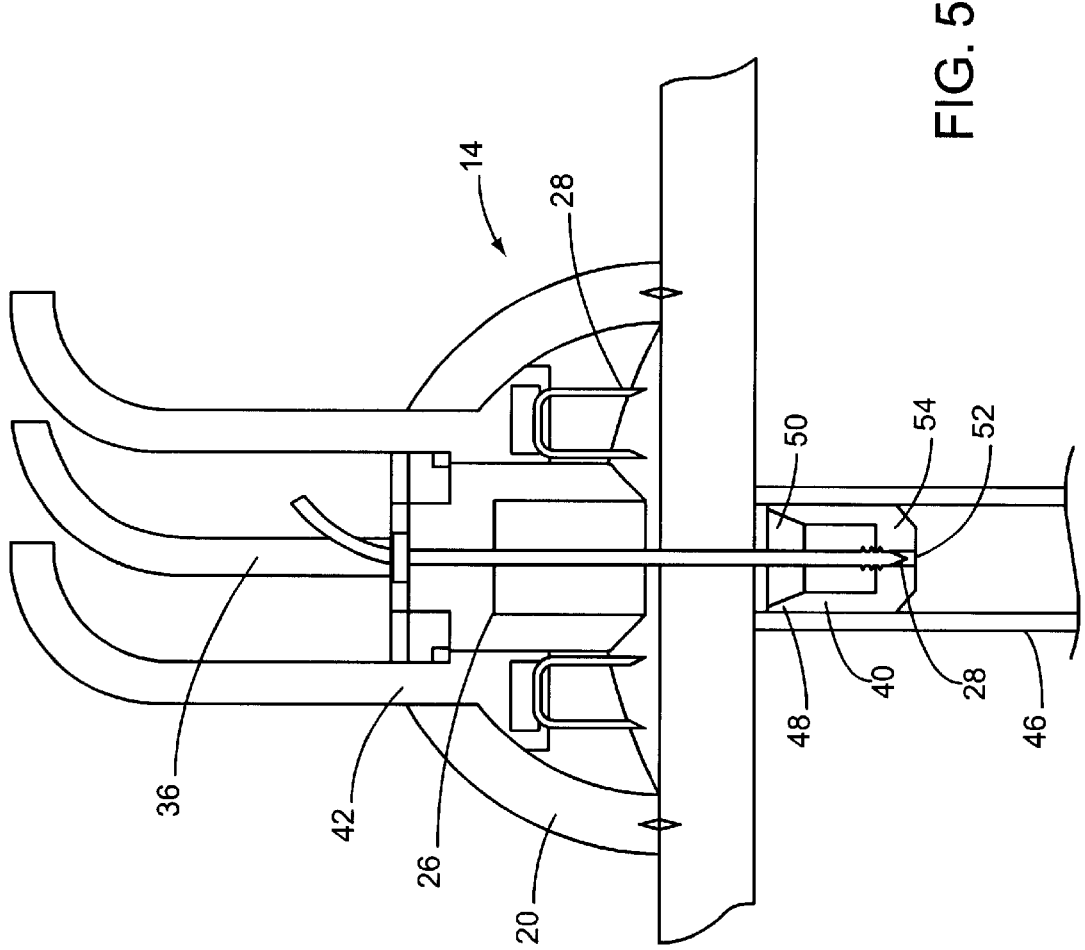
FIG. 5 is a perspective view of the distal end portion of a surgical anastomosis device illustrating a further step in the surgical procedure in accordance with the first embodiment.
Figure 6:
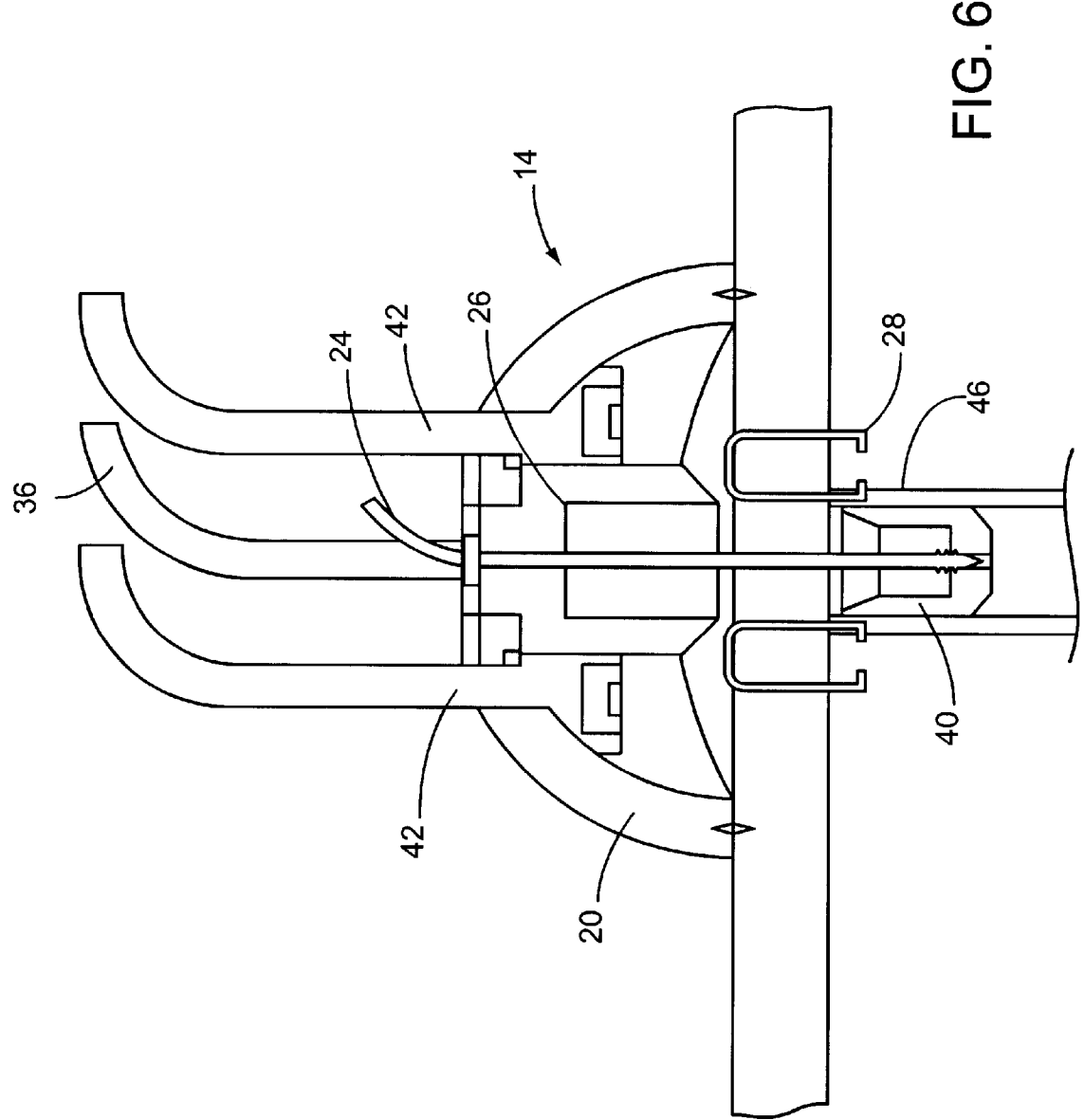
FIG. 6 is a perspective view of the distal end portion of a surgical anastomosis device illustrating a further step in the surgical procedure in accordance with the first embodiment.
Figure 7:
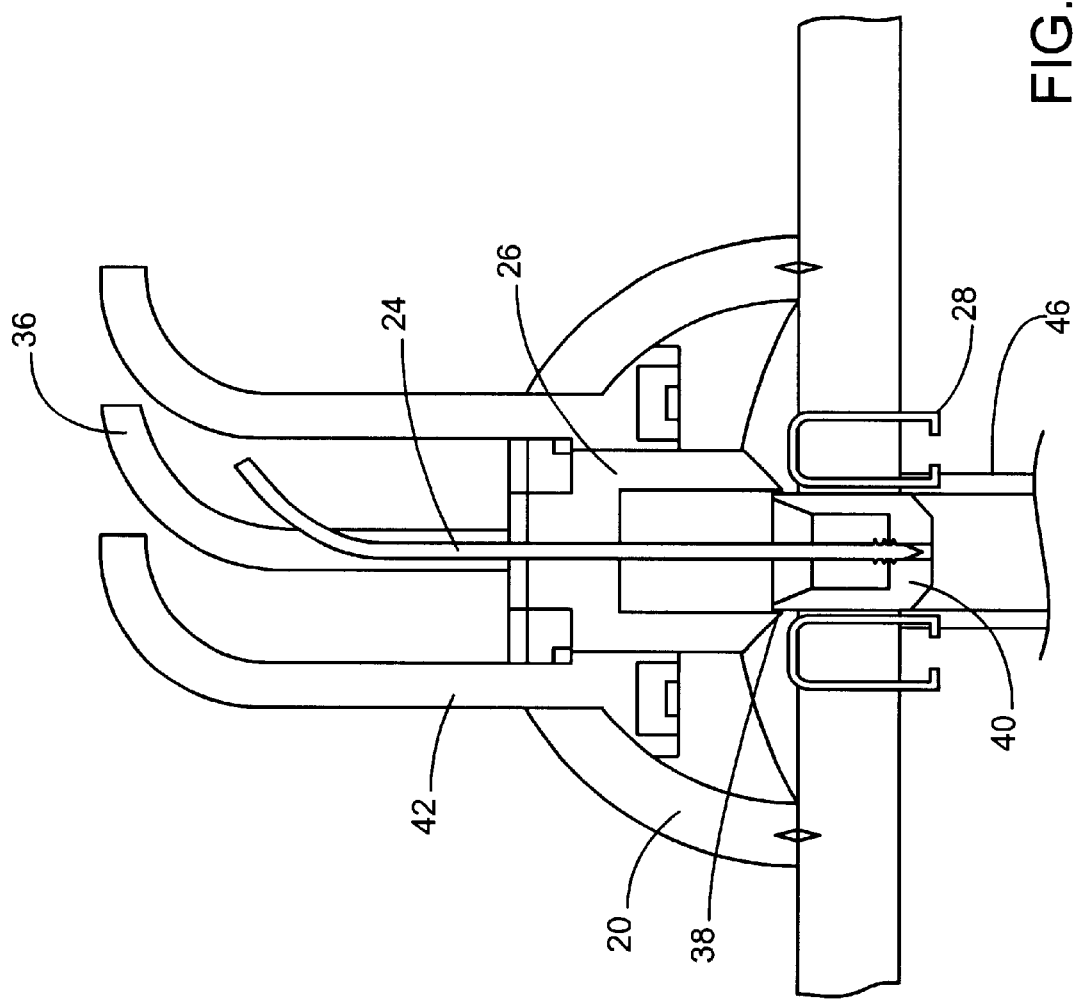
FIG. 7 is a perspective view of the distal end portion of a surgical anastomosis device illustrating a further step in the surgical procedure in accordance with the first embodiment.
Figure 8:
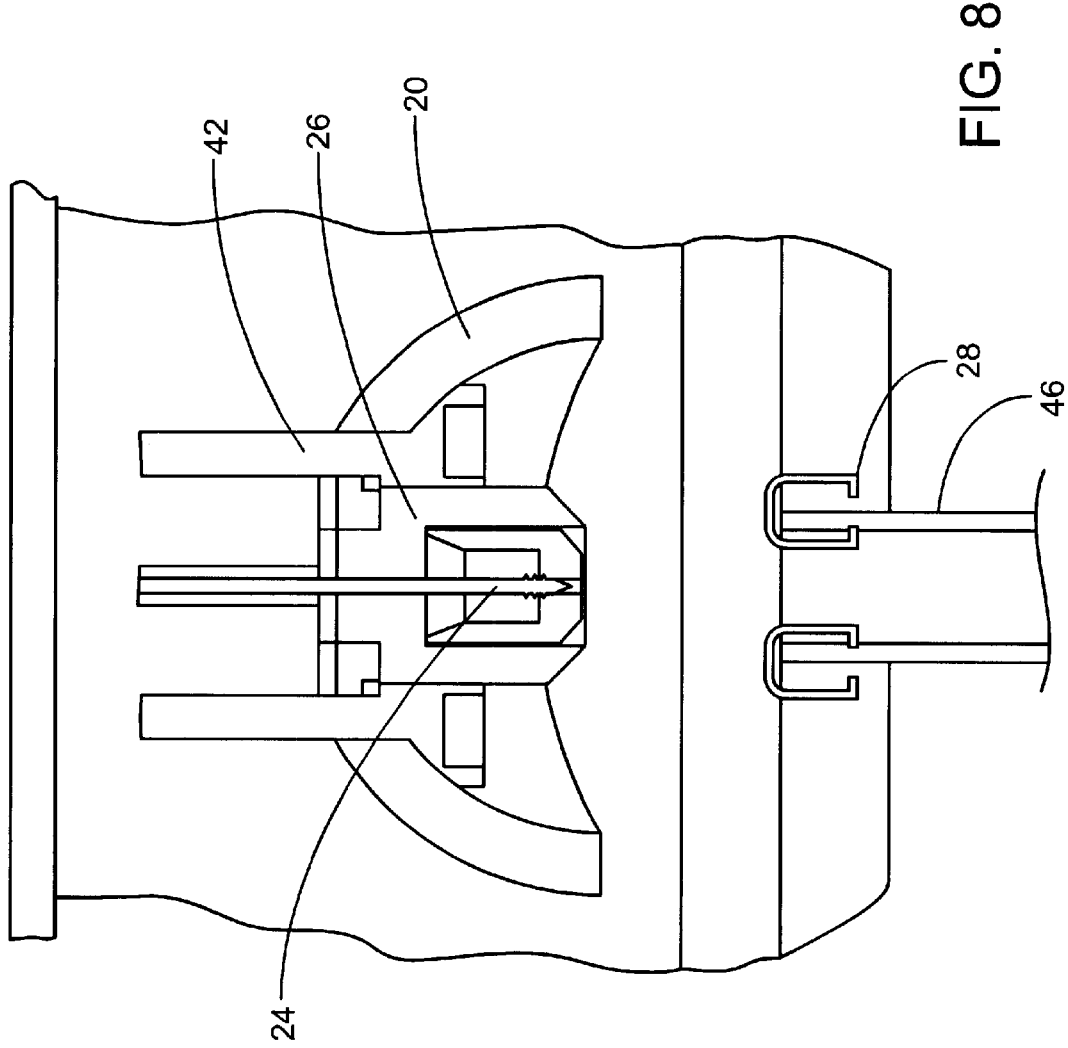
FIG. 8 is a perspective view of the distal end portion of a surgical anastomosis device illustrating a further step in the surgical procedure in accordance with the first embodiment.
Figure 9:
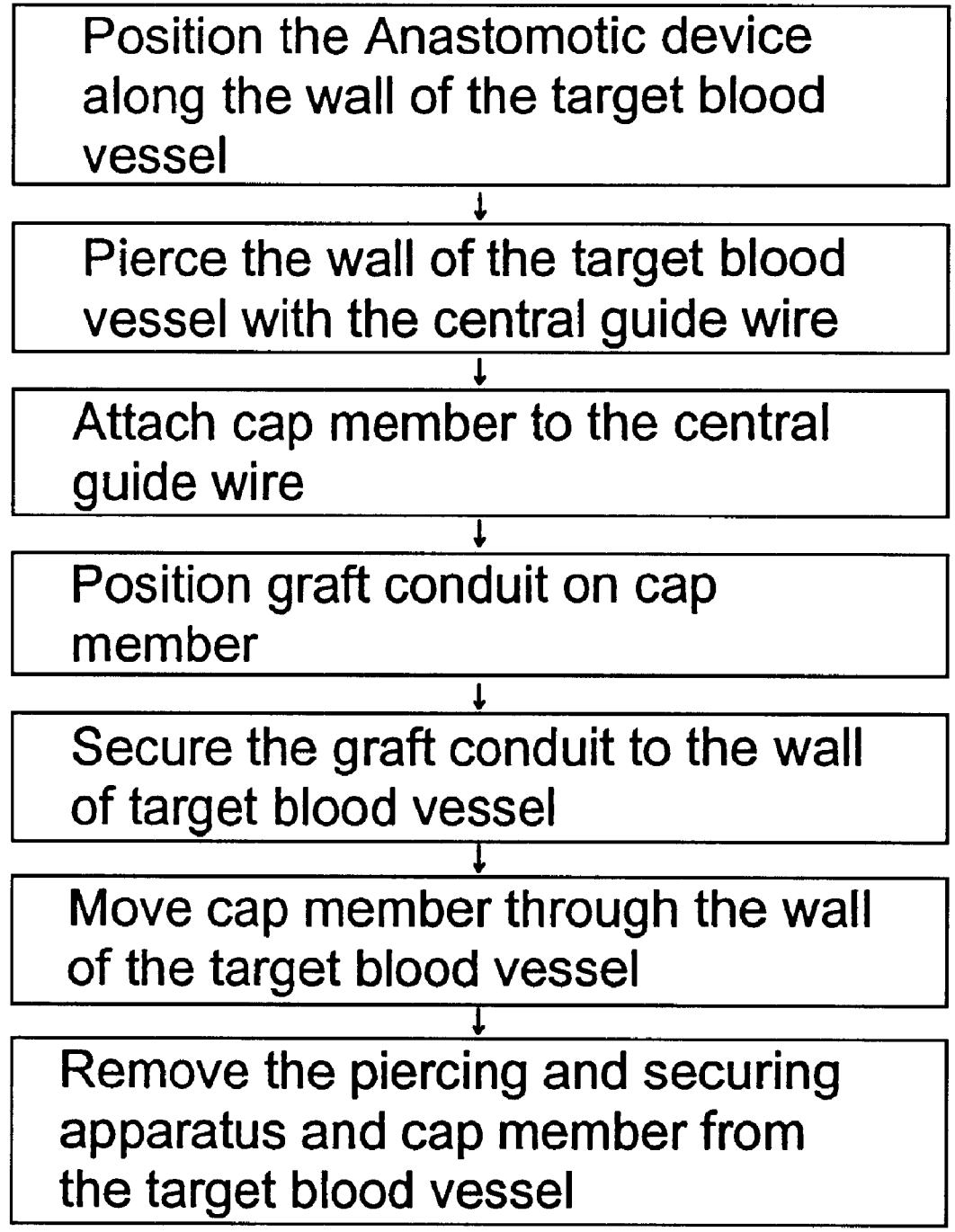
FIG. 9 is a flow chart of the method of performing an anastomosis using the surgical anastomosis device of the first embodiment of the present invention.

The first embodiment of the present invention is illustrated in connection with FIGS. 1–9. The anastomosis device 10 includes a delivery apparatus 12, piercing and securing apparatus 14 and an external assembly 16. The delivery apparatus 12 is preferably a controlling, precurved or guiding flexible catheter 18 that has at least one tubular wall of a fixed length with a proximal end portion for entry and a distal end portion for egress of the piercing and securing apparatus. The flexible catheter is preferably steerable for the delivery of the distal end portion to the desired location in the target blood vessel. Although the flexible catheter is preferably a conventionally available member, it may be modified for use in combination with the piercing and securing apparatus 14 described below such that the proximal end portion may include the various components that are used to actuate the elements of the piercing and securing apparatus 14 once the distal end portion of the flexible catheter is position at the desired location in the target blood vessel. Additionally, it is anticipated that the combined delivery apparatus and piercing and securing apparatus may be formed so that the entire device is inserted into the target blood vessel through a cannula or similar member and then operated as described below while the teachings of conventional catheters are utilized to direct the distal end portion of the delivery device to the desired location along the wall of the target blood vessel.

As shown, the piercing and securing apparatus 14 preferably includes a cap shaped assembly having an outer ovoid, semi-ovoid or semicircular member 20 that may be flexible or semi rigid as desired. The periphery of the semicircular member 20 may include a plurality of anchoring members 22 that are used to engage the tissue of the wall of the target blood vessel and retain or anchor the semicircular member in the desired location along the wall of the target blood vessel. The semicircular member 20 also preferably encircles the distal end portions of the central guide wire 24 and the cap engaging member 26 as well as the staples 28. Each of the central guide wire 24 and the cap engaging member 26 and the staples 28 are movable relative to each other and relative to the wall of the target blood vessel in response to movement of actuation members associated with the proximal end portion of the flexible catheter 18. The central guide wire 24 is an elongate and semi rigid member that preferably includes a sharpened piercing portion 30 thereon. Additionally, the distal end portion of the central guide wire preferably includes a surface such as a notched or threaded surface 32 that may be frictionally or otherwise engaged by a portion of the external apparatus as described below. Therefore, the distal end portion of the central guide wire 24 may be shaped to pierce the wall of the target blood vessel by the direct application of force through the central guide wire 24 or the central guide wire may be twisted in a manner such that the piercing portion 30 on the distal end portion of the central guide wire is threaded through the wall of the target blood vessel. The central guide wire 24 is preferably centrally positioned to ensure that the central guide wire pierces the desired location on the wall of the target blood vessel when the semicircular member 20 is in the desired position. The central guide wire is also independently movable with respect to the distal end portion of the flexible catheter and the cap engaging member 26 in response to movement of a control member on the proximal end portion of the delivery apparatus 12. Additionally, as shown, the central guide wire may include a stop member 34 or other element a predetermined distance from the distal end portion of the central guide wire 24 to ensure that the central guide wire is not extended too far beyond the distal end portion of the semicircular member 20.

The cap engaging member 26 of the present invention is preferably a generally cylindrical member having a proximal end portion which is substantially closed and a generally open distal end portion. The proximal end portion of the cap engaging member 26 includes an opening therethrough to enable the central guide wire 24 to be movably passed therethrough. An elongate proximal connector 36 is fixedly attached to the proximal end portion of the cap engaging member and extends between the proximal end portion of the cap engaging member 26 and the proximal end portion of the delivery apparatus 12 to enable the movement of the cap engaging member to be controlled externally of the patient and independently of the central guide wire 24 and semicircular member 20. The distal end portion of the cap engaging member 26 has an opening therein that is sized to engage a cutting member such as cap member 40 of the external assembly 16 therein as described below. The circumferential edge 38 of the distal end portion of the cap engaging member 26 may optionally be sharpened to assist to in the removal of a portion of the wall of the target blood vessel as described more fully below. The distal end portion of the cap engaging member 26 generally encircles the central guide wire and is adjacent to the staples 28 and staple delivery mechanism 42 as described below.

The staples 28 are positioned adjacent to the exterior of the cap engaging member 26 and along the interior of the semicircular member 20. In a preferred form of the present invention, two or more staples 28 are used to provide a secure engagement between the graft conduit and the wall of the target blood vessel. It is anticipated that fewer staples 28 are required if it is desired to merely retain the graft conduit along the wall of the target while the graft conduit is externally secured, such as by suturing or adhesive bonding, to the wall of the blood vessel. If the staples are intended to be the primary form of attachment between the graft conduit and the wall of the target blood vessel, more staples may be utilized. The staples 28 are preferably of a generally conventional shape for medical use wherein the staples 28 have an overall U-shape with a sharpened distal end portion. It is anticipated that barbs may be used on the distal end portion to provide an even more secure connection between the graft conduit and the wall of the target blood vessel. Additionally, the staples may be formed of a non-allergenic resorbable or non-resorbable material depending on whether or not the staples are intended to be the primary source of attachment or are merely a temporary attachment prior to the suturing or application of an adhesive material. The staple delivery mechanism 42 preferably consists of one or more elongate members that extend between the proximal end portion of the delivery apparatus 12 and the interior of the semicircular member 20. As shown, the distal end portion of the staple delivery mechanism is enlarged to abut against a portion of the interior of the semicircular member and further includes a staple retainer 44 to retain the staple 28 thereon prior to the insertion of the staple into the wall of the target blood vessel. In a preferred form of this invention, the staple retainer 44 consists of a flexible ledge member that has sufficient rigidity to retain the staple in the desired orientation as the staple is pushed into the wall of the target blood vessel while also having sufficient flexibility to deform and release the staple when the staple engages the tissue in the wall of the target blood vessel.

In this embodiment, the external assembly 16 preferably consists of the generally cylindrically shaped cap member 40. The external surface of the cap member 40 is preferably sized to frictionally retain the graft conduit 46 thereon. Additionally, the cap member 40 may include an area thereon to allow one or more sutures to pass therethrough to allow for the temporary attachment of the graft conduit thereto. The interior of the cap member 40 includes a sharpened cutting surface 48 extending along the periphery of the first surface 50 of the cap member 40 and a small opening 52 along the second surface 52 of the cap member 40. The small opening 54 is preferably threaded or otherwise shaped to securely engage the threaded portion 32 of the central guide wire 24 therein. It is anticipated that the engagement between the small opening 52 and the threaded portion 32 will be sufficient to allow the cap member 40 to be easily attached to the central guide wire while also being sufficiently secure to allow the cap member to be drawn through the tissue of the wall of the target blood vessel and out of the body of the patient as described more fully below.

The first embodiment of the present invention preferably includes the initial step of passing the delivery apparatus 12 and piercing and securing apparatus 14 through the target vessel to the desired location against the desired wall of the target vessel. If anchor members 22 are utilized on the semicircular member 20, they are deployed into the wall of the target blood vessel. The central guide wire 24 is then moved distally relative to the semicircular member 20 and cap engaging member 26 of the piercing and securing apparatus 14 until the central guide wire 24 passes through the wall of the target vessel and the stop member reaches the proximal end portion of the cap engaging member 26. In this position, the central guide wire 24 extends a short distance beyond the outer surface of the wall of the target blood vessel. The previously prepared graft conduit 46 is then positioned over the cap member 40, central guide wire 24 and the anastomosis site adjacent to the exterior surface of the target blood vessel. Next, the graft conduit 46 is frictionally or otherwise secured to the outer surface of the cap member 40. The cap member 40 is then temporarily secured to the threaded portion 32 on the second surface 54 of the central guide wire adjacent to the outer surface of the to target vessel. The first surface 50 of the cap member 40 is then moved into contact with the outer wall of the target blood vessel by withdrawing the central guide wire 24 relative to the remaining components of the piercing and securing apparatus 14 to position the distal end portion of the graft adjacent to the inner surface of the target blood vessel. The staples are then moved into contact with the inner surface of the wall of the target blood vessel and once the proper orientation of the graft conduit 46 is verified adjacent to the outer surface of the target blood vessel, the staples advanced by moving the staple delivery mechanism relative to the semicircular member 20 until the staples pierce through the wall of the target blood vessel. In one form of the present embodiment, the ends of the staples may then be manipulated to ensure that the end portion of the graft conduit is pierced and secured by the staples 28. The staples 28 are then released from the distal end portion of the staple delivery mechanism 42 by withdrawing the staple delivery mechanism relative to the semicircular member 20 until the staple retainers flex and release the staples 28 therefrom. The fluid tight attachment of the graft conduit to the wall of the target blood vessel may then be verified, created or reinforced by suturing or bonding as described above. The central guide wire 24 may then be withdrawn to pull the cap member 40 through the wall of the target blood vessel. As this occurs, the cutting surface 48 on the first surface 50 of the cap member 40 preferably cuts the tissue of the portion of the wall of the target blood vessel that is located along the interior of the graft conduit 46. The cutting of the tissue is preferably assisted by the edges 38 of the cap engaging member 26 to cleanly cut the tissue in a manner similar to a pair of scissors. The first surface 50 of the cap member 40 is then drawn into the distal end portion of the cap engaging member 26. The cap engaging member and cap member encloses any tissue that is cut from the wall of the target blood vessel. Once the cap member is positioned adjacent to the distal end portion of the cap engaging member, the entire assembly, including the cap member 40 and the piercing and securing apparatus 14 are withdrawn from the target blood vessel. Therefore, the staples 28 and graft conduit 46 remain in the desired position adjacent to the wall of the target blood vessel. If the other end of the graft conduit 46 is to be attached to another location on the wall of the target blood vessel to complete the bypass procedure, a new piercing and securing apparatus 14 may be used or the staples 28 may be replaced in the device used above and the distal end portion of the delivery apparatus and/or the piercing and securing apparatus may be relocated to the desired location on the wall of the target blood vessel.

Figure 10:
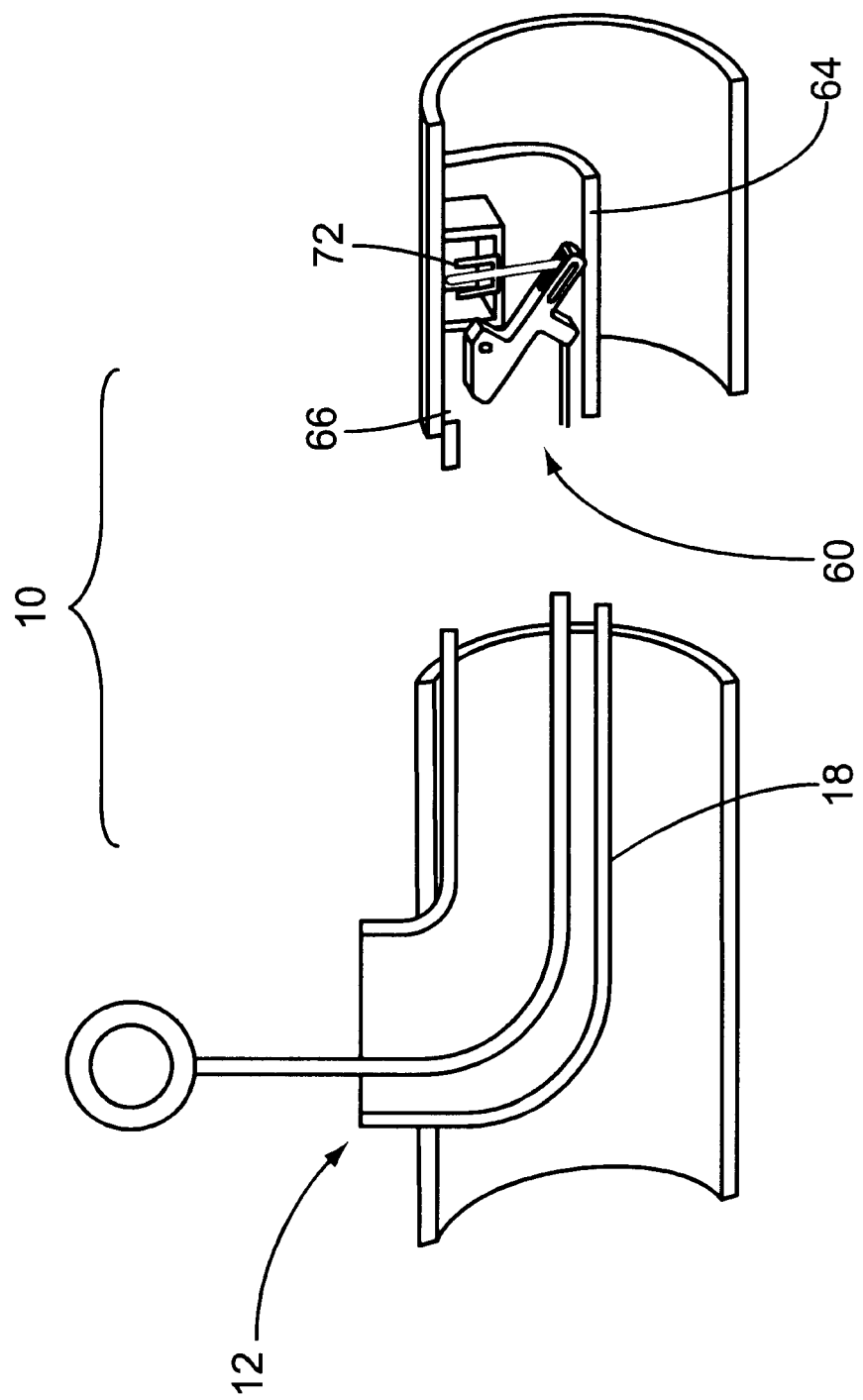
FIG. 10 is a perspective view of a surgical anastomosis device in accordance with a second embodiment of the invention.
Figure 11:
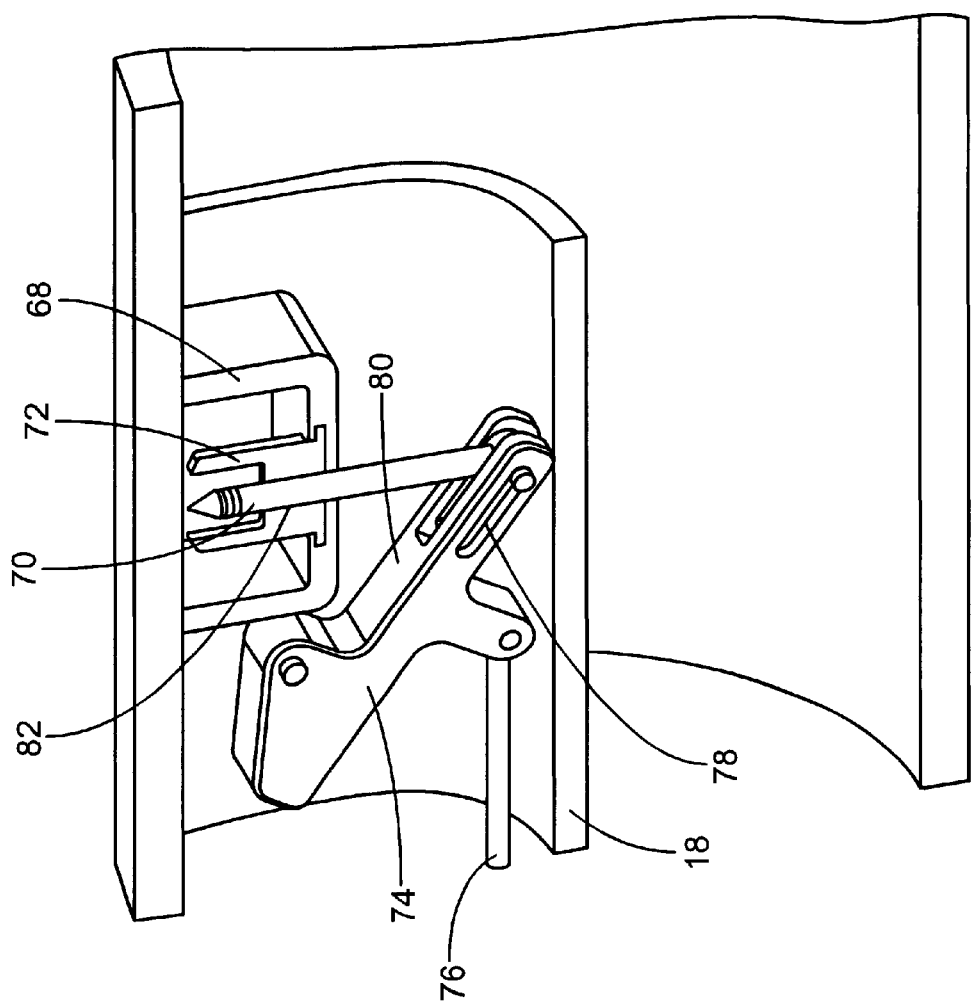
FIG. 11 is a perspective view of the distal end portion of a surgical anastomosis device illustrating a surgical procedure in accordance with the second embodiment.
Figure 12:
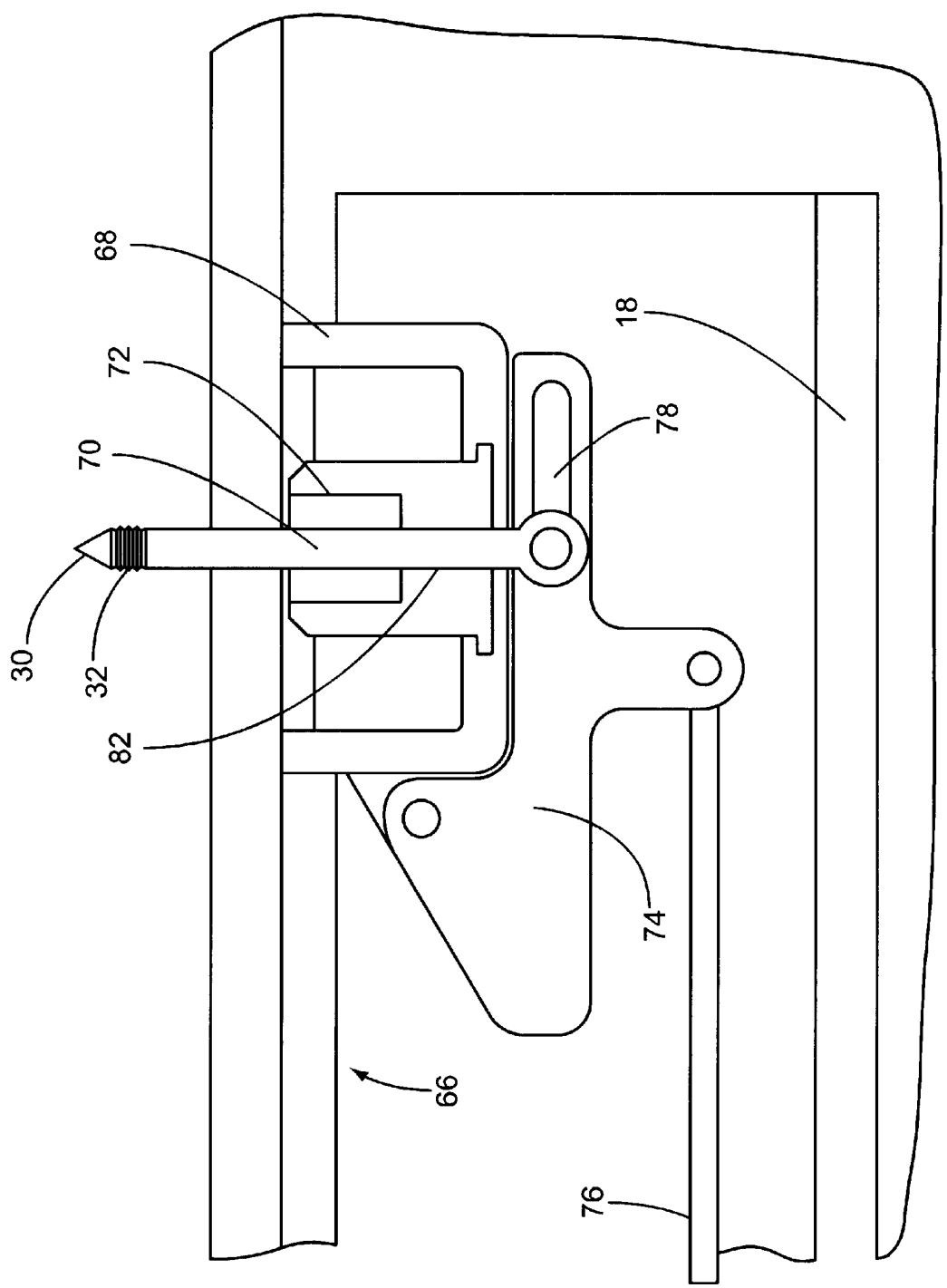
FIG. 12 is a perspective view of the distal end portion of a surgical anastomosis device illustrating a further step in the surgical procedure in accordance with the second embodiment.
Figure 13:
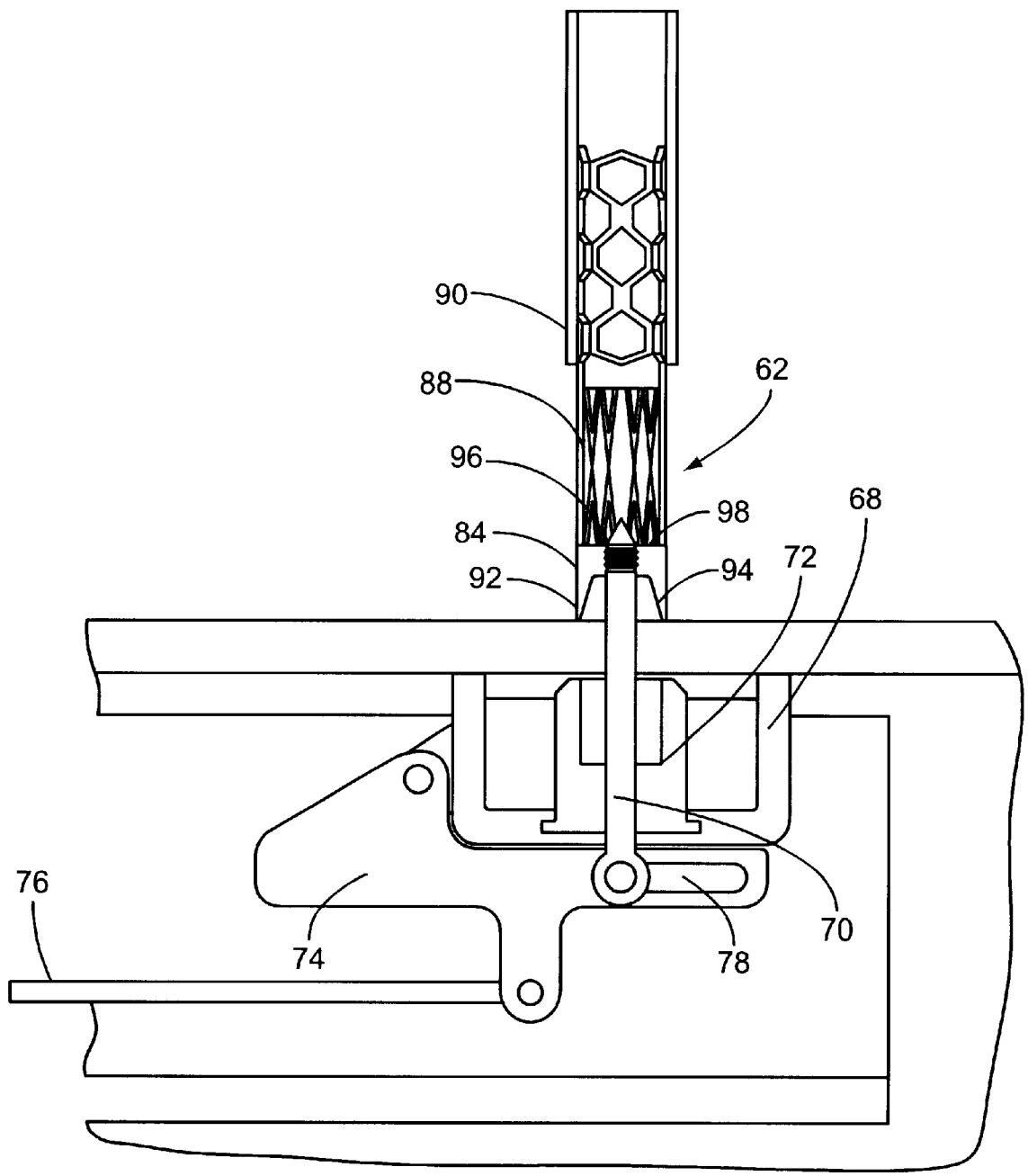
FIG. 13 is a perspective view of the distal end portion of a surgical anastomosis device illustrating a further step in the surgical procedure in accordance with the second embodiment.
Figure 14:
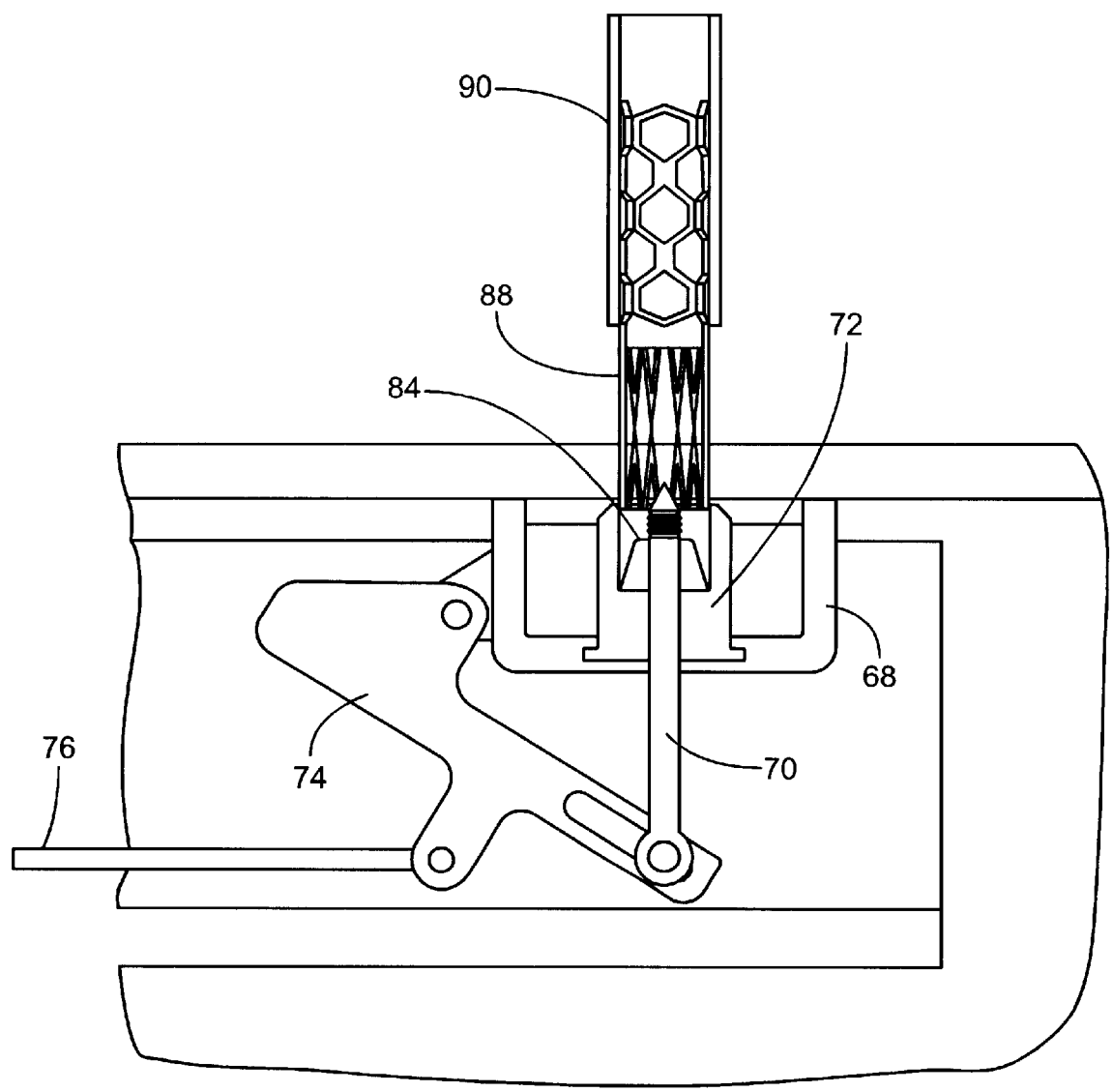
FIG. 14 is a perspective view of the distal end portion of a surgical anastomosis device illustrating a further step in the surgical procedure in accordance with the second embodiment.
Figure 15:
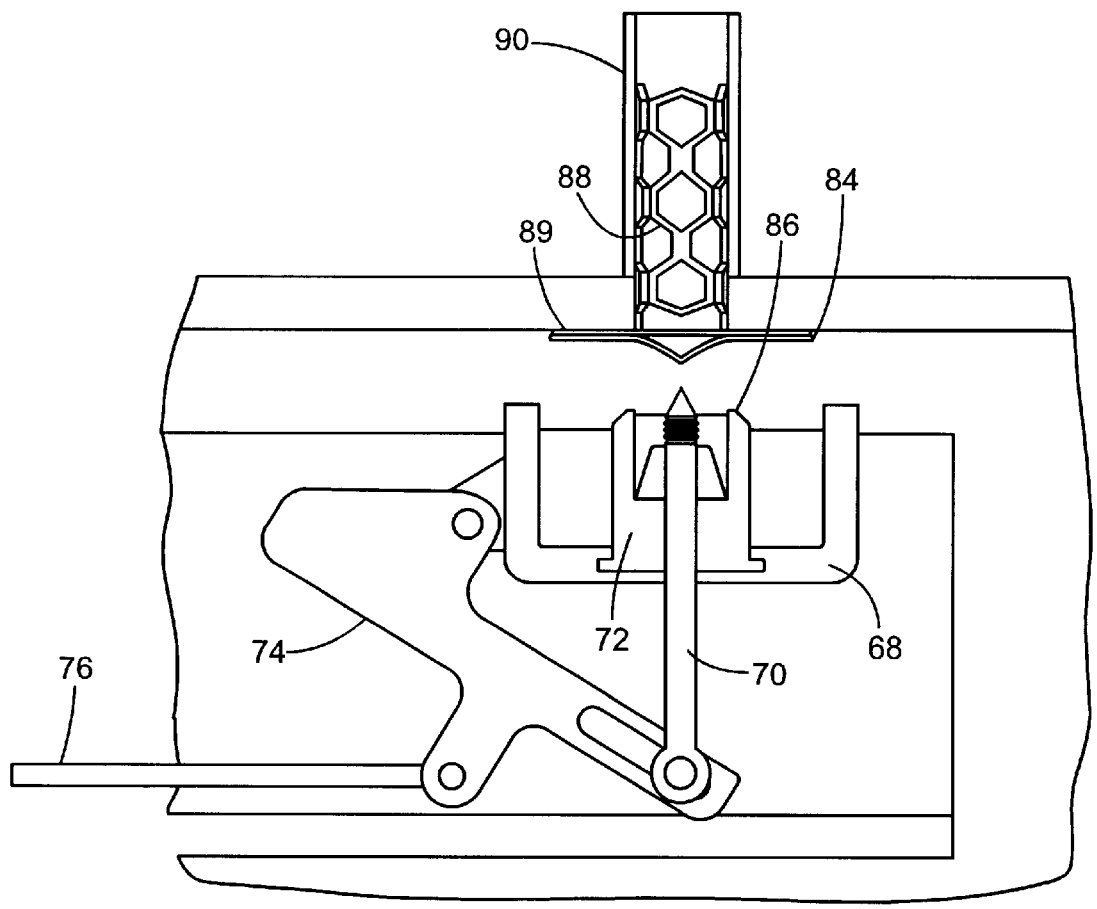
FIG. 15 is a perspective view of the distal end portion of a surgical anastomosis device illustrating a further step in the surgical procedure in accordance with the second embodiment.
Figure 16:
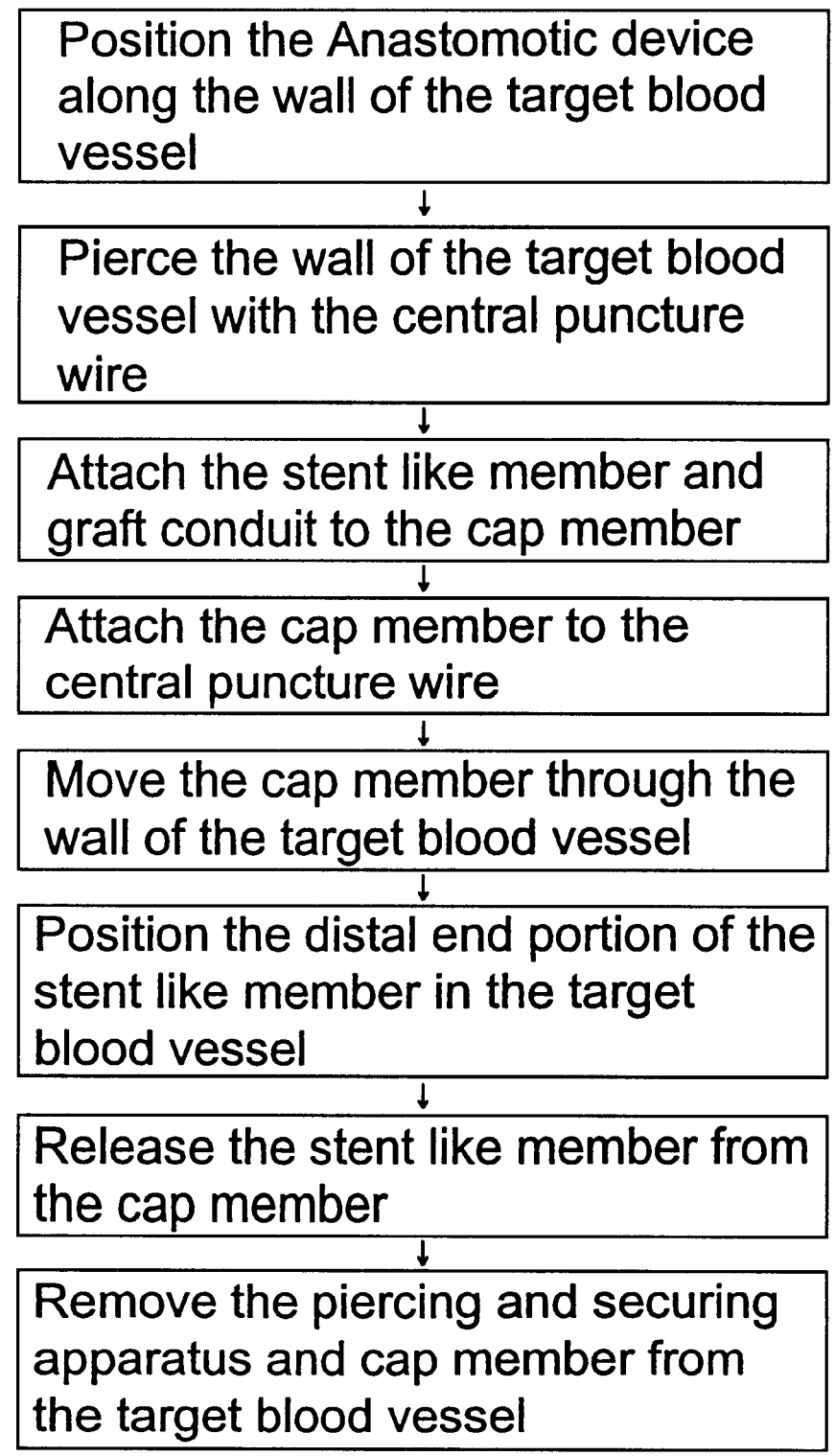
FIG. 16 is a flow chart of the method of performing an anastomosis using the surgical anastomosis device of the second embodiment of the present invention.

The second embodiment of the present invention is illustrated in connection with FIGS. 10–16. For the sake of brevity and to more clearly describe the preferred forms of the present invention, common numbers are used herein to refer to common components. The anastomosis device 10 of this second embodiment includes a delivery apparatus 12, piercing and securing apparatus 60 and an external assembly 62. The delivery apparatus 12 is preferably a controlling, precurved or guiding flexible catheter 18 that has at least one tubular wall of a fixed length with a proximal end portion for entry and a distal end portion for egress of the piercing and securing apparatus. The flexible catheter 18 is preferably steerable for the delivery of the distal end portion to the desired location in the target blood vessel. Although the flexible catheter is preferably a conventionally available member, it may be modified for use in combination with the piercing and securing apparatus 60 described below such that the proximal end portion may include the various components that are used to actuate the elements of the piercing and securing apparatus 60 once the distal end portion of the flexible catheter is positioned at the desired location in the target blood vessel. Additionally, it is anticipated that a combined delivery apparatus and piercing and securing apparatus may be formed so that the entire device is inserted into the target blood vessel through a cannula or similar member and then operated as described below while the teachings of conventional catheters are utilized to direct the distal end portion of the delivery device to the desired location along the wall of the target blood vessel. For example, the combined device may consist basically of a steerable catheter having the components of the piercing and securing apparatus therein and the catheter portion of the combined device includes a distally extending portion 64 having an open sidewall 66 that is positioned at the desired location adjacent to the wall of the target blood vessel. In this form of the present embodiment, the piercing and securing apparatus 60 extends through the sidewall 66 of the catheter in a manner similar to the method using the semicircular member 20 described above.

As shown, the piercing and securing apparatus 60 of this embodiment preferably) includes a cap shaped member having an outer generally cylindrical or semicircular member 68 that may be flexible or semi rigid as desired. The periphery of the semicircular member 68 may include a plurality of anchoring members (not shown) that are used to engage the tissue of the wall of the target blood vessel and retain or anchor the semicircular member in the desired location along the wall of the target blood vessel. The semicircular member 68 also preferably encircles the distal end portions of the central puncture wire 70 and a cap engaging member 72. The central puncture wire 70 of this embodiment is preferably movable relative to the semicircular member 68 and the cap engaging member 72 as well as being movable relative to the wall of the target blood vessel in response to movement of an actuation member associated with the proximal end portion of the flexible catheter 18. The central puncture wire 70 of the present embodiment is preferably pivotally connected to the outer surface of the semicircular member 68 as well as to the actuatable member associated with the proximal end portion of the flexible catheter. The central puncture wire 70 is preferably an elongate and semi rigid member that includes a sharpened piercing portion 30 thereon. Additionally, the distal end portion of the central puncture wire 70 preferably includes a surface such as a threaded surface 32 that may be engaged by a portion of the external apparatus as described below. Therefore, the distal end portion of the central puncture wire 70 may be shaped to pierce the wall of the target blood vessel by the direct application of force through the central puncture wire 70 through a pivoting mechanism 74 attached between the proximal end portion of the central puncture wire 70 and the outer surface of the semicircular member upon movement of the pivoting mechanism 74 as an elongate and semi rigid control wire 76 is moved distally and proximally with respect to the reminder of the piercing and securing apparatus and the flexible catheter. The central puncture wire 70 is preferably centrally positioned with respect to the semicircular member 68 and cap engaging member 72 to ensure that the central puncture wire 70 pierces the desired location on the wall of the target blood vessel when the semicircular member 68 is in the desired position along the wall of the target blood vessel.

Additionally, as shown, the central puncture wire 70 includes the pivoting mechanism 74 that functions as a stop member to allow the central puncture wire 70 to move a predetermined distance from the cap engaging member 72 to ensure that the central puncture wire 70 is not extended too far beyond the distal end portion of the semicircular member 68. The pivoting mechanism 74 includes a bar member 80 having a slotted attachment area 78 to allow the proximal end portion of the central puncture wire 70 to be slidably and pivotally connected to the bar member 80. The bar member is also pivotally connected to the outer surface of the semicircular member 68. The control wire 76 is pivotally connected to an extension located approximately midway along the lengthwise dimension of the bar member 80 to provide a push/pull type of force to the central puncture wire 70. In this embodiment, the cap engaging member 72 also includes an elongate and preferably central located opening 82 on the proximal surface thereof to ensure that the central puncture wire moves generally linearly with respect to the tissue of the target blood vessel. Similarly, the semicircular member 68 includes a relatively small diameter and centrally positioned opening therein to allow the central puncture wire 70 to extend therethrough The cap engaging member 72 of the present invention is preferably a generally cylindrical member having a proximal end portion which is substantially closed and a generally open distal end portion. The proximal end portion of the cap engaging member 72 includes the central opening 82 therethrough to enable the central guide wire 70 to be slidably passed therethrough in response to movement of the control wire 76. In this embodiment, a proximally positioned actuator controls the movement of the control wire 76 from the proximal end portion of the delivery apparatus 12 to enable the movement of the central puncture wire 70 to be controlled externally of the patient and in combination with combined limited movement of the cap engaging member 72 and the semicircular member 68. The distal end portion of the cap engaging member 72 has an opening therein that is sized to engage a cutting member such as cap member 84 of the external assembly 62 therein as described below. The cap engaging member includes a circumferential edge 86 on the distal end portion thereof. The circumferential edge 86 of the cap engaging member 72 may optionally be sharpened to assist in the removal of a portion of the wall of the target blood vessel as described more fully below. The distal end portion of the cap engaging member 72 generally encircles the central puncture wire 70 and is generally encircled by the semicircular member 68.

In this embodiment, the external assembly 62 preferably consists of the generally cylindrically shaped cap member 84, a stent-like member 88. and graft conduit 90. The external surface of the cap member 84 is preferably sized to frictionally retain the distal end portion of the stent-like member 88 thereon. The external surface of the stent-like member 88 is preferably sized to frictionally retain the distal end portion of the graft conduit 90 thereon. Additionally, the stent-like member 88 may include an area thereon to allow one or more sutures to pass therethrough to allow for the attachment of the graft conduit along a first portion thereof. The second portion of the stent like member 88 is preferably radially expandable so that a plurality of wing members 89 may extend therefrom. In one form of the stent like member 88, the stent like member may be formed of a nitinol type material that automatically expands in response to certain predetermined conditions, such as temperature. Additionally, the stent like member 88 may be formed such that the wing members are manually or otherwise radially expandable such that the interior of the wall of the target blood vessel is engaged thereby upon the expansion of the wing members 89. Similarly, first portion of the stent like member may be made of a nitinol or otherwise expandable material to assist in retaining the graft conduit 90 thereon.

The interior of the cap member 84 includes a sharpened cutting surface 92 extending along the periphery of the first surface 94 of the cap member 84 and a small opening 96 along the second surface 98 of the cap member 84. The small opening 96 is preferably threaded or otherwise shaped to securely engage the threaded portion 32 of the central puncture wire 70 therein. It is anticipated that the engagement between the small opening 96 and the threaded portion 32 will be sufficient to allow the cap member 84 to be easily attached to the central puncture wire 70. The cap member 84 is also secured to the central puncture wire 70 in a manner that is sufficient to allow the cap member 84 to be drawn through the tissue of the wall of the target blood vessel and out of the body of the patient as described more fully below.

The second embodiment of the present invention preferably includes the initial step of passing the delivery apparatus 12 and piercing and securing apparatus 60, individually or in combination, through the target vessel to the desired location against the desired wall of the target vessel. The semicircular member 68 is then deployed at the desired location along the wall of the target blood vessel. The central puncture wire 70 is then moved distally relative to the semicircular member 68 and cap engaging member 72 of the piercing and securing apparatus 60 until the central puncture wire 70 passes through the wall of the target vessel. In the present embodiment, this is accomplished by moving the control wire 76 distally to cause the bar member 80 to pivot with respect to the semicircular member 68 and the cap engaging member 72. When the bar member 80 reaches the proximal end portion of the cap engaging member 72 and semicircular member 68, the distal movement of the central puncture wire 70 is stopped. In this position, the central puncture wire 70 extends a short distance beyond the outer surface of the wall of the target blood vessel. The cap member 84 is then secured to the threaded portion of the central puncture wire 70. The previously prepared graft conduit 90 is then positioned over the stent-like member 88 and the first portion of the stent-like member 88 may be expanded as desired to retain the graft conduit thereon. The second portion of the stent like member 88 may then be releasably attached to the second surface 98 of the cap member 84 and the cutting surface 92 of the cap member 84 is oriented along the anastomosis site adjacent to the exterior surface of the target blood vessel. The first surface 94 of the cap member 84 is then moved into contact with the outer wall of the target blood vessel by withdrawing the control wire 76 relative to the remaining components of the piercing and securing apparatus 60. The fluid tight attachment of the graft conduit to the wall of the target blood vessel may then be verified, created or reinforced by suturing or bonding as described above. The central puncture wire 70 may then be withdrawn to pull the cap member 84 through the wall of the target blood vessel. As this occurs, the cutting surface 92 on the first surface 94 of the cap member 84 preferably cuts the tissue of the portion of the wall of the target blood vessel that is located along the interior of the graft conduit 90. The cutting of the tissue is preferably assisted by the edges of the cap engaging member 72 to cleanly cut the tissue in a manner similar to a pair of scissors. The first surface 94 of the cap member 84 is then drawn into the distal end portion of the cap engaging member 72. The cap engaging member and cap member encloses any tissue that is cut from the wall of the target blood vessel.

The proximal movement of the control wire 76 also causes the second portion of the stent like member 88 to be drawn through the wall of the target blood vessel. If the second portion of the stent like member 88 is formed of a nitinol type of material, the wing members 89 may be designed to radially expand as the stent like member is warmed by the blood of the patient in the target blood vessel. Alternately, the wing members 89 may be manually expanded at this time to engage the wall of the inner surface of the target blood vessel. In either event, the expansion of the wing members 89 may be designed to automatically release the stent like member 88 from the cap member 84. Alternately, the size of the inner surface of the cap engaging member 72 may be chosen so as to cause the stent like member 88 to release from the cap member 84 as the cap members 84 is drawn into the interior of the cap engaging member 72. Similarly, the stent like member 88 may be threadedly or otherwise releasably secured to the cap member 84 to allow the user to selectively release the stent like member 88 from the cap member 84 as desired when the wing members 89 of the stent like member 88 are properly positioned in the target blood vessel. Thereafter, the delivery apparatus 12, piercing and securing apparatus 60 and the cap member 84 may be removed from the target blood vessel while the stent like member 88 and graft conduit 90 remain in the desired position to complete the first or second part of the bypass. In the event that the user desires to secure the remaining part of the graft conduit to another location, the piercing and securing apparatus may be moved to the desired location in the target blood vessel and the steps set forth above may be repeated.

While this invention has been particularly shown and described with references to preferred embodiments thereof, it will be understood by those skilled in the art that various changes in form and details may be made therein without departing from the spirit and scope of the invention as defined by the appended claims.

What is claimed:

1. A catheter system for creating a bypass between a target blood vessel having an interior and exterior wall surface in a patient and a graft conduit, said system comprising:

an elongate guide member having a distal end portion and a proximal end portion wherein said distal end portion is threadable through the target blood vessel and includes a tissue penetrating member thereon to penetrate the interior wall surface of the target blood vessel and an attachment member adjacent thereto;

a generally cylindrical cap member having an external surface and a tissue penetrating surface to penetrate the exterior wall surface of the target blood vessel and said cap member further including an attachment surface wherein the attachment surface is sized to releasably engage the attachment member of said guide member and said tissue penetrating surface includes a generally open portion that is oriented to face said proximal end portion of said guide member;

a generally cylindrical stent-like member having a distal end portion and a proximal end portion wherein the distal end portion is attachable to the cap member and the proximal end portion is spaced apart therefrom; and an elongate graft conduit having a first end portion thereon and said first end portion is attachable to said proximal end portion of said stent like member.

2. The system of claim 1 wherein the guide member includes a cap engaging member associated therewith and the cap engaging member includes a first surface thereon and the cap member and the cap engaging member are movable relative to each other such that at least a portion of the cap member is receivable in the cap engaging member and the tissue penetrating member is movable to a position which is adjacent to the first surface of the cap engaging member.

3. The system of claim 2 wherein the first surface of said cap engaging member is sized to enclose at least the tissue penetrating member and a portion of the cap member when the cap member and the tissue penetrating member are oriented adjacent to each other.

4. The system of claim 1 wherein the distal end portion of the stent like member is releasably attachable to the exterior surface of the cap member and the graft conduit is fixedly attachable to the proximal end portion of the stent like member.

5. The system of claim 1 wherein at least part of the distal end portion of the stent like member is laterally movable with respect to the proximal end portion thereof.

6. The system of claim 5 wherein the distal end portion of said stent like member includes a plurality of wing members that are movable between a first position wherein the distal end portion of the stent like member is in a generally cylindrical configuration and a second position wherein said at least part of the distal end portion of the stent like member extends laterally therefrom a sufficient distance to engage the interior surface of the wall of the target blood vessel.

7. The system of claim 6 wherein the proximal end portion of the stent like member extends beyond the exterior surface of the target blood vessel and includes the graft conduit attached thereto.

8. The system of claim 1 wherein at least a portion of the stent like member is radially expandable.

9. The system of claim 1 wherein the tissue penetrating member is a pointed member and the attachment member is a threaded member.

10. The system of claim 1 wherein the tissue penetrating surface of the cap member is a conical surface to dilate the exterior wall surface of the target blood vessel.

11. The system of claim 1 wherein the tissue penetrating surface is a sharpened surface to penetrate and remove a portion of the exterior wall surface of the target blood vessel.

12. The system of claim 1 further including a generally semicircular member and the tissue penetrating member is movable relative thereto and the semicircular member encircles the tissue penetrating member in a first position of the tissue penetrating member.

13. The system of claim 12 wherein the semicircular member is sized to abut against the interior wall surface of the target blood vessel and said semicircular member includes a plurality of anchor members thereon to extend into the interior wall surface of the target blood vessel.

14. A catheter system for creating a bypass between a target blood vessel having an interior and exterior wall surface in a patient and a graft conduit, said system comprising:

an elongate guide member having a distal end portion which is passable through the target blood vessel and a proximal end portion wherein said distal end portion includes a tissue penetrating member thereon to penetrate the interior wall surface of the target blood vessel to create an opening therethrough and an attachment member adjacent thereto;

a generally cylindrical cap engaging member including a first surface thereon and the cap engaging member and guide member are movable relative to each other and the tissue penetrating member is movable to a position which is spaced apart from the first surface of the cap engaging member;

a generally cylindrical cap member which is attachable to the cap engaging member along the exterior surface of the target blood vessel and having an external surface and an open first end portion and a generally closed second end portion wherein said first end portion includes a tissue penetrating surface thereon to penetrate the exterior wall surface of the target blood vessel and said cap member further including an attachment surface associated with said second end portion of said cap member wherein the attachment surface is sized to releasably engage the attachment member of said guide member and said tissue penetrating surface is oriented to face said first surface of said cap engaging member and wherein the cap engaging member and said cap member are movable relative to each other to form an opening in the target blood vessel therebetween; and an elongate graft conduit having a first end portion thereon which is operatively secured to the cap member and is movable into contact with the outer surface of the target blood vessel.

15. The system of claim 14 further including a plurality of staples wherein said staples are movable through the interior wall surface of the target blood vessel into engagement with the first end portion of said graft conduit.

16. The system of claim 15 further including a staple delivery mechanism generally adjacent to an exterior portion of the cap engaging member and wherein said staple delivery mechanism is movable independently of the cap engaging member and said guide member.

17. The system of claim 14 further including a stent like member having a generally cylindrical configuration and including distal end portions and proximal end portions wherein the graft conduit is attachable to said proximal end portion of said stent like member and said cap member is attachable to said distal end portion of said stent like member.

18. The system of claim 17 wherein said distal end portion of said stent like member is movable between a first position that is generally aligned with the proximal end portion and a second position wherein the distal end portion extends generally laterally from said proximal end portion to engage the interior wall surface of the target blood vessel.

19. The system of claim 17 wherein the proximal end portion of the stent like member is radially expandable.

20. The system of claim 17 wherein said distal end portion of said stent like member is laterally extendable.

21. The system of claim 14 wherein the cap engaging member is movable to a position wherein the first surface thereof is adjacent to the tissue penetrating surface of the cap member.

22. The system of claim 14 wherein the cap engaging member includes an open first end portion and a generally closed second end portion wherein said first end portion is adjacent to the first surface thereof and the cap engaging member and guide member are movable relative to each other to draw said tissue penetrating surface toward the first surface of the cap engaging member and through the exterior surface of the wall of the target blood vessel.

23. The method of performing an anastomosis in the wall of a target blood vessel including the steps of:

positioning an elongate member having a piercing and securing device thereon and wherein the piercing and securing device is positioned in a target blood vessel so the distal end portion thereof is in a desired position along the interior surface of the wall of the target blood vessel and a proximal end portion of the elongate member is spaced apart from the desired position along the interior surface of the target blood vessel and which extends outwardly of the target blood vessel;

causing the movement of a blood vessel penetrating member so the penetrating member passes from the interior surface of the wall of the target blood vessel to a location beyond the exterior surface of the wall to form an opening therein;

attaching a separate cap member to the penetrating member and causing the cap member to pass from the exterior surface of the wall of the target blood vessel to a location adjacent to the interior surface of the wall of the target blood vessel and adjacent to the piercing and securing device on the elongate member thereby forming an opening in the wall of the target blood vessel and causing a graft conduit to be positioned in fluid communication with the opening in the wall of the target blood vessel; and withdrawing the cap member and piercing and securing device through the target blood vessel from a location that is spaced apart from the graft conduit.

24. The method of claim 23 further including the step of attaching the graft conduit to a stent like member wherein at least a portion of the stent like member is drawn through the opening in the wall of the target blood vessel as the cap member is drawn therethrough and the graft conduit is secured to at least a portion of the stent like member as the graft conduit is brought into fluid communication with the opening in the wall of the target blood vessel.

25. The method of claim 24 further including the step of causing a portion of the stent like member to extend laterally to engage at least a portion of the wall of the target blood vessel adjacent to the opening in the wall of the target blood vessel.

26. The method of claim 23 further including the step of causing a plurality of staples to pass from the interior surface of the wall of the target blood vessel to engage at least a portion of the graft conduit.

27. The method of claim 23 further including the step of causing the blood vessel penetrating member to dilate the opening of the target blood vessel by drawing the cap member through the wall of the target blood vessel.

28. The method of claim 23 further including the step of increasing the size of the opening in the wall of the blood vessel by causing a cutting surface thereon to pass through the wall of the target blood vessel.

29. The method of claim 28 further including the step of causing the cutting surface to be positioned adjacent a portion of a cap engaging member and withdrawing the cap member and cap engaging member from the target blood vessel.

30. The method of claim 23 further including the step of attaching the graft conduit to a stent like member wherein at least a portion of the stent like member is drawn through the opening in the wall of the target blood vessel as the cap member is drawn therethrough and the graft conduit is secured to at least a portion of the stent like member as the graft conduit is brought into fluid communication with the opening in the wall of the target blood vessel and then causing a portion of the stent like member to release form the cap member and extend laterally to engage at least a portion of the wall of the target blood vessel adjacent to the opening in the wall of the target blood vessel.

31. The method of claim 23 including the further steps of positioning an elongate piercing and securing device in a target blood vessel so the distal end portion thereof is in a desired position along the interior surface of the wall of the target blood vessel and the proximal end portion thereof extends outwardly of the target blood vessel;

causing the movement of a blood vessel penetrating member so the penetrating member passes from the interior surface of the wall of the target blood vessel to a location beyond the exterior surface of the wall to form a further opening therein;

attaching a cap member to the penetrating member and causing the cap member to pass from the exterior surface of the wall of the target blood vessel to a location adjacent to the interior surface of the wall of the target blood vessel thereby forming an enlarged opening in the wall of the target blood vessel and causing a second end of a graft conduit to be positioned in fluid communication with the enlarged opening in the wall of the target blood vessel; and withdrawing the cap member and piercing and securing device from the target blood vessel.

\* \* \* \* \*